United States Patent
Cole, Jr.

(10) Patent No.: US 10,328,220 B2
(45) Date of Patent: Jun. 25, 2019

(54) BI-DIRECTIONAL FLOW GENERATION IN AN IN-EXSUFFLATION SYSTEM

(71) Applicant: KONINKLIJKE PHILIPS N.V., Eindhoven (NL)

(72) Inventor: Kenneth E. Cole, Jr., New Alexandria, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 808 days.

(21) Appl. No.: 14/386,472

(22) PCT Filed: Mar. 18, 2013

(86) PCT No.: PCT/IB2013/052138
§ 371 (c)(1),
(2) Date: Sep. 19, 2014

(87) PCT Pub. No.: WO2013/140321
PCT Pub. Date: Sep. 26, 2013

(65) Prior Publication Data
US 2015/0027444 A1   Jan. 29, 2015

Related U.S. Application Data

(60) Provisional application No. 61/613,721, filed on Mar. 21, 2012.

(51) Int. Cl.
*A61M 16/00* (2006.01)
*A61M 16/08* (2006.01)
*A61M 16/20* (2006.01)

(52) U.S. Cl.
CPC .... *A61M 16/0009* (2014.02); *A61M 16/0051* (2013.01); *A61M 16/0066* (2013.01);
(Continued)

(58) Field of Classification Search
CPC .......... A61M 16/0009; A61M 16/0069; A61M 16/202; A61M 16/0883; A61M 16/0066;
(Continued)

(56) References Cited

U.S. PATENT DOCUMENTS 5,373,842 A   12/1994   Olsson
7,810,497 B2  10/2010   Pittman
(Continued)

FOREIGN PATENT DOCUMENTS

CA   2230622 A1 *   9/1998   ............ A61M 16/00
CN   1764486 A       4/2006
(Continued)

*Primary Examiner* — Gregory A Anderson
*Assistant Examiner* — Margaret M Luarca
(74) *Attorney, Agent, or Firm* — Michael W. Haas (57) ABSTRACT

A bi-directional gas flow generation system (10), the system comprising: (a) a pressure generator (14) comprising an inlet (40) and an outlet (42), (b) a flow member (16) comprising an outlet port (50), an inlet port (52), a respiratory circuit port (54) and a flow path (60), (c) a first valve (18), (d) a second valve (20), and (e) a processor (24) configured to selectively control the first valve and the second valve to operate in (i) a first mode in which gas flows from the flow member inlet port (52) to the respiratory circuit port (54), thereby creating a positive pressure at the respiratory circuit port (54) to insufflate the subject; and (ii) a second mode in which gas flows from the respiratory circuit port (54) to the flow member outlet port (50), thereby facilitating gas flow out from the airway of the subject to exsufflate the subject.

16 Claims, 5 Drawing Sheets (52) U.S. Cl.
CPC .... *A61M 16/0069* (2014.02); *A61M 16/0883* (2014.02); *A61M 16/202* (2014.02); *A61M 2205/52* (2013.01)

(58) Field of Classification Search
CPC .......... A61M 16/0051; A61M 16/0003; A61M 16/08; A61M 16/0816; A61M 16/0875; A61M 16/00; A61M 16/0078; A61M 16/01; A61M 16/0833; A61M 16/0858; A61M 16/101; A61M 16/1015; A61M 16/12; A61M 16/203; A61M 16/204; A61M 16/205; A61M 2016/0015; A61M 2016/0027
USPC ............ 128/200.24, 204.18, 204.22, 204.23, 128/205.13, 205.14, 205.24
See application file for complete search history.

(56) References Cited

U.S. PATENT DOCUMENTS

| | | |
|---|---|---|
| 8,118,024 B2 | 2/2012 | DeVries |
| 2002/0014239 A1* | 2/2002 | Chalvignac ........... A61M 16/20 128/204.18 |
| 2006/0213511 A1 | 9/2006 | Hansen |

FOREIGN PATENT DOCUMENTS

| | | |
|---|---|---|
| CN | 101489615 A | 7/2008 |
| CN | 101448539 A | 6/2009 |
| EP | 0862922 A1 | 9/1998 |
| JP | 4054378 U | 5/1992 |
| JP | 11992307070 A | 10/1992 |
| WO | WO2012001621 A1 | 1/2012 |

* cited by examiner

BI-DIRECTIONAL FLOW GENERATION IN AN IN-EXSUFFLATION SYSTEM

CROSS-REFERENCE TO RELATED APPLICATIONS

This patent application claims the priority benefit under 35 U.S.C. § 371 of international patent application No. PCT/IB2013/052138, filed Mar. 18, 2013, which claims the priority benefit under 35 U.S.C. § 119(e) of U.S. Provisional Application No. 61/613,721 filed on Mar. 21, 2012, the contents of which are herein incorporated by reference.

BACKGROUND OF THE INVENTION

1. Field of the Invention

The present disclosure pertains to the generation of a bi-directional flow of breathable gas for inexsufflating a subject through a respiratory circuit.

2. Description of the Related Art

Various pressure support and/or artificial airway clearance systems that provide pressure support therapy and/or airway clearance to the airway of a subject are known.

Artificial airway clearance may be achieved via many methods. One such method employs the use of a mechanical in-exsufflator (MI-E). A MI-E is a medical device that delivers positive airway pressure through the mouth, nose, or a tracheostomy, gently filling the lungs to capacity (insufflation). It then abruptly reverses pressure which generates an expiratory flow, mimicking a cough (exsufflation).

In conventional pressure support and/or inexsufflation systems, proper gas generation and delivery timing is accomplished through mechanically intertwined valving.

SUMMARY OF THE INVENTION

Accordingly, one or more aspects of the present disclosure relate to a bi-directional gas flow generation system. The system comprises a pressure generator configured to generate a pressurized flow of breathable gas for delivery to the airway of a subject. The pressure generator comprises an inlet configured to receive breathable gas into the pressure generator, and an outlet configured to output the pressurized flow of breathable gas from the pressure generator. The bi-directional gas flow generation system further comprises a flow member configured to communicate with the pressure generator and a respiratory circuit. The flow member comprises an outlet port coupled with the pressure generator inlet, an inlet port coupled with the pressure generator outlet, a respiratory circuit port coupled with the respiratory circuit, and a flow path that places the respiratory circuit port in fluid communication with the flow member outlet port and the flow member inlet port. The bi-directional gas flow generation system further comprises a first valve configured to selectively control flow through the flow path between the respiratory circuit port and the flow member outlet port, a second valve that is mechanically separate and discreet from the first valve, and is configured to selectively control flow through the flow path between the flow member inlet port and the respiratory circuit port, and a processor. The processor is configured to selectively control the first valve and the second valve to operate in (i) a first mode in which gas flows from the flow member inlet port to the respiratory circuit port, thereby creating a positive pressure at the respiratory circuit port to insufflate the subject; and (ii) a second mode in which gas flows from the respiratory circuit port to the flow member outlet port, thereby facilitating gas flow out from the airway of the subject to exsufflate the subject.

Yet another aspect of the present disclosure relates to a method of generating a bi-directional flow of gas. The method comprises generating a pressurized flow of breathable gas by receiving breathable gas into a pressure generator via a pressure generator inlet and outputting the pressurized flow of breathable gas from the pressure generator via a pressure generator outlet; selectively controlling flow between a respiratory circuit and the pressure generator inlet with a first valve; selectively controlling flow between the pressure generator outlet and the respiratory circuit with a second valve that is mechanically separate and discreet from the first valve; and selectively controlling the first valve and the second valve to operate in (i) a first mode in which gas flows from the pressure generator outlet to the respiratory circuit, thereby creating a positive pressure in the respiratory circuit to insufflate the subject; and (ii) a second mode in which gas flows from the respiratory circuit to the pressure generator inlet, thereby facilitating gas flow out from the airway of the subject to exsufflate the subject.

Still another aspect of present disclosure relates to a bi-directional gas flow generation system. The system comprises means for generating a pressurized flow of breathable gas for delivery to the airway of a subject. The means for generating comprises means for receiving breathable gas into the means for generating and means for outputting the pressurized flow of breathable gas from the means for generating. The system further comprises means for providing fluid communication between a respiratory circuit and the means for receiving and the means for outputting, first means for selectively controlling flow between the respiratory circuit and the means for receiving, second means, mechanically separate and discreet from the first means, for selectively controlling flow between the respiratory circuit and the means for outputting, and means for selectively controlling the first means and the second means to operate in (i) a first mode in which gas flows from the means for outputting, to the respiratory circuit, thereby creating a positive pressure in the respiratory circuit to insufflate the subject; and (ii) a second mode in which gas flows from the respiratory circuit to the means for receiving, thereby facilitating gas flow out from the airway of the subject to exsufflate the subject.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
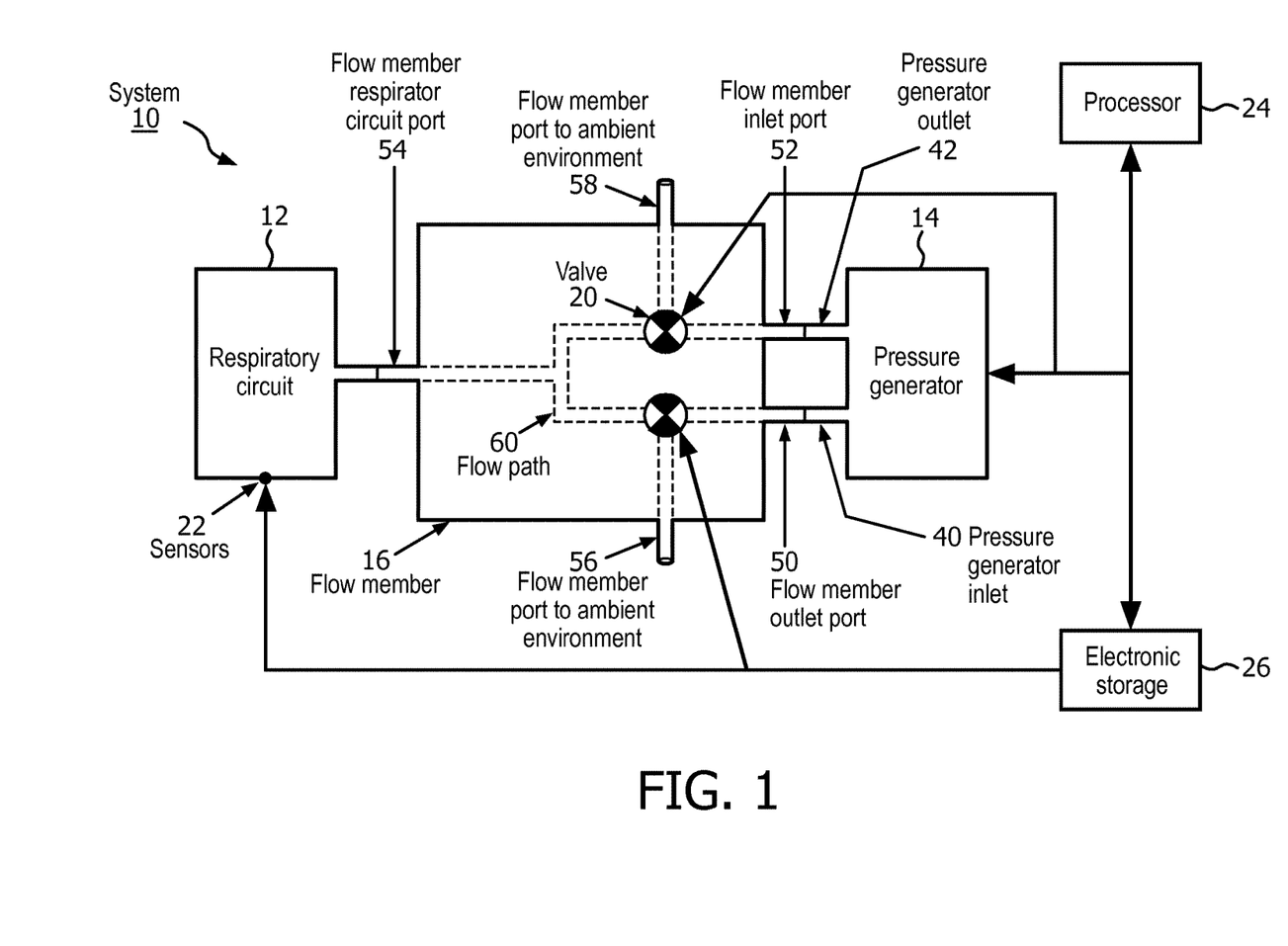
FIG. 1 is a schematic of a system configured to generate a bi-directional flow of gas.

FIG. 1 schematically illustrates a system 10 configured to generate a bi-directional pressurized flow of breathable gas to inexsufflate a subject through a respiratory circuit 12. In one embodiment, system 10 comprises one or more of a pressure generator 14, a flow member 16, a first valve 18, a second valve 20, one or more sensors 22, a processor 24, electronic storage 26, and/or other components. In particular, system 10 generates the bi-directional flow by operating the two valves 18, 20 to communicate the flow of breathable gas through flow member 16 between pressure generator 14 and respiratory circuit 12.

Respiratory circuit 12 is configured to deliver the pressurized flow of breathable gas to the airway of the subject. Respiratory circuit 12 may be configured for inexsufflation and/or other pressure support therapy. As such, respiratory circuit 12 comprises one or more conduits, an interface appliance, and/or other components. The conduit may be configured to convey the pressurized flow of gas to the interface appliance. The interface appliance may be configured to deliver the flow of gas to the airway of a subject. In some embodiments, the interface appliance is non-invasive. As such, the interface appliance non-invasively engages the subject. Non-invasive engagement comprises removably engaging an area (or areas) surrounding one or more external orifices of the airway of the subject (e.g., nostrils and/or mouth) to communicate gas between the airway of the subject and the interface appliance. Some examples of non-invasive interface appliances may comprise, for example, a nasal cannula, a nasal mask, a nasal/oral mask, a full face mask, a total face mask, or other interface appliances that communicate a flow of gas with an airway of a subject. The present disclosure is not limited to these examples, and contemplates delivery of the flow of gas to the subject using any interface appliance.

Pressure generator 14 is configured to provide a pressurized flow of breathable gas for delivery to the airway of a subject. Pressure generator 14 is configured to deliver the pressurized flow of gas via respiratory circuit 12, flow member 16, and/or other devices. Pressure generator 14 receives a flow of gas from a gas source, such as the ambient atmosphere, and elevates the pressure of that gas for delivery to the subject via respiratory circuit 12, and/or other devices. In some embodiments, pressure generator 14 receives the flow of gas through an inlet 40 coupled to flow member 16 and first valve 18, and delivers the gas through an outlet 42 coupled to flow member 16 and second valve 20 as shown in FIG. 1.

Pressure generator 14 is configured such that one or more gas parameters of the pressurized flow of breathable gas are controlled in accordance with a therapy regime. The one or more gas parameters may include, for example, one or more of flow, pressure, humidity, velocity, acceleration, and/or other parameters. In some embodiments, system 10 is a device dedicated to mechanical inexsufflation. In some embodiments, pressure generator 14 is a ventilator and/or positive airway pressure device configured to provide therapy other than and/or in addition to inexsufflation. Pressure generator 14 is any device, such as, for example, a pump, blower, piston, or bellows, that is capable of elevating the pressure of the received gas for delivery to a patient. The present disclosure contemplates controlling the operating speed of the blower, for example, either alone or in combination with valve 18, valve 20, flow member 16, and/or other devices, to control the pressure and/or flow of gas provided to respiratory circuit 12. The present disclosure also contemplates that gas other than ambient atmospheric air may be introduced into system 10 for delivery to the patient.

By way of a non-limiting example, pressure generator 14 may be configured to adjust the parameters of the pressurized flow of breathable gas in accordance with an inexsufflation therapy regime. In one embodiment, the therapy regime may dictate that the pressurized flow of breathable gas is delivered to the airway of a subject via respiratory circuit 12 at a first pressure level during insufflation. The first pressure level is sufficiently high that the lungs of the subject are at least partially filled during insufflation. After insufflation, valve 18, valve 20, and flow member 16 may cooperate with pressure generator 14 to reduce the pressure of the pressurized flow of breathable gas with sufficient abruptness that expiratory flow through the airway of the subject is sufficient to remove mucus and/or other debris from the airway and/or lungs of the subject. The pressure may be reduced from the first pressure level to a second pressure level that is substantially lower than the first pressure level. The second pressure level may, for example, be a negative pressure. After expiration is complete, valve 18, valve 20, and flow member 16 may operate to return the pressure of the pressurized flow of breathable gas to the first pressure level to facilitate another inspiration in preparation for another inexsufflation. After a series of inexsufflations, inexsufflation may be ceased.

Flow member 16 is configured to communicate the flow of gas between pressure generator 14 and respiratory circuit 12. Flow member 16 defines a gas flow pathway between pressure generator outlet 42 and respiratory circuit 12, and respiratory circuit 12 and pressure generator inlet 40. Flow member 16 comprises an outlet port 50, an inlet port 52, a respiratory circuit port 54, two ports 56, 58 to the ambient atmosphere, a flow path 60, and/or other components. In some embodiments, pressure generator inlet 40 is coupled to flow member outlet port 50 and pressure generator outlet 42 is coupled to flow member inlet port 52. In some embodiments, coupling may comprise a removable attachment. In some embodiments, coupling may be accomplished through added plumbing and/or additional manufactured parts to couple the devices.

In some embodiments, pressure generator inlet 40 is directly connected to flow member outlet port 50 and pressure generator outlet 42 is directly connected to flow member inlet port 52. The direct connection between pressure generator 14 and flow member 16 may reduce and/or eliminate the need for added plumbing and/or additional manufactured parts to couple the devices. The direct connection between pressure generator 14 and flow member 16 may allow pressure generator 14, flow member 16, valve 18, valve 20, and/or other components to be arranged in a tight geometric arrangement under a single housing.

Outlet port 50 is configured to couple to pressure generator inlet 40. Inlet port 52 is configured to couple to pressure generator outlet 42. Respiratory circuit port 54 is configured to couple to respiratory circuit 12. Flow member port 56 to the ambient atmosphere is configured such that the blower, for example, of pressure generator 14 may draw breathable gas into flow member 16 and pressure generator 14 from the ambient atmosphere through valve 18 for inhalation. Flow member port 58 to the ambient atmosphere is configured such that pressure generator 14 may output exhaled gas through flow member 16 and valve 20 to the ambient atmosphere. Flow path 60 is configured to place respiratory circuit port 54 in fluid communication with flow member outlet port 50 and flow member inlet port 52.

Valve 18 is configured to selectively control flow through flow path 60 between respiratory circuit port 54 and flow member outlet port 50. In some embodiments, valve 18 may comprise one or more valves in series and/or in parallel. Examples of valves and/or other pressure regulating devices suitable for use as valve 18 comprise, a plug valve, a ball valve, a check valve, a butterfly valve, a solenoid, and/or other pressure regulating devices The pressure regulating devices mentioned above and/or other pressure regulating devices that may be used as valve 18 may be controlled magnetically, hydraulically, pneumatically, via an electric motor and/or another mode of control configured to open and/or close a valve and/or other pressure control device.

Valve 20 is configured to selectively control flow through flow path 60 between flow member inlet port 52 and respiratory circuit port 54. Valve 20 may be housed in the same manifold as valve 18 but is mechanically separate and discreet from valve 18. In some embodiments, valve 20 may comprise one or more valves in series and/or in parallel. Examples of valves and/or other pressure regulating devices suitable for use as valve 20 comprise, a plug valve, a ball valve, a check valve, a butterfly valve, a solenoid, and/or other pressure regulating devices The pressure regulating devices mentioned above and/or other pressure regulating devices that may be used as valve 20 may be controlled magnetically, hydraulically, pneumatically, via an electric motor and/or another mode of control configured to open and/or close a valve and/or other pressure control device.

Sensors 22 are configured to generate output signals conveying information related to one or more gas parameters of the gas within system 10. The one or more gas parameters comprise flow, volume, pressure, a composition (e.g., concentration(s) of one or more constituents), temperature, humidity, acceleration, velocity, acoustics, changes in a parameter indicative of respiration, and/or other gas parameters. Sensors 22 may comprise one or more sensors that measure such parameters directly (e.g., through fluid communication with the flow of gas in respiratory circuit 12). Sensors 22 may comprise one or more sensors that generate output signals related to one or more parameters of the flow of gas indirectly. For example, one or more of sensors 22 may generate an output based on an operating parameter of pressure generator 14 (e.g., motor current, voltage, rotational velocity, and/or other operating parameters), and/or other parameters. Although sensors 22 are illustrated at a single location within (or in communication with) respiratory circuit 12, this is not intended to be limiting. Sensors 22 may include sensors disposed in a plurality of locations, such as for example, within pressure generator 14, within (or in communication with) flow member 16, and/or other locations.

Processor 24 is configured to provide information processing capabilities in system 10. As such, processor 24 may comprise one or more of a digital processor, an analog processor, a digital circuit designed to process information, an analog circuit designed to process information, a state machine, and/or other mechanisms for electronically processing information. Although processor 24 is shown in FIG. 1 as a single entity, this is for illustrative purposes only. In some implementations, processor 24 may comprise a plurality of processing units. These processing units may be physically located within the same device (e.g., pressure generator 14), or processor 24 may represent processing functionality of a plurality of devices operating in coordination.

Processor 24 is configured to selectively control valve 18 and valve 20 to operate in a first mode and a second mode. In the first mode gas flows from pressure generator 14, through flow member inlet port 52, to respiratory circuit port 54, thereby creating a positive pressure at respiratory circuit port 54 (e.g., for insufflation). In the first mode, flow member 16 directs gas from the ambient atmosphere, via valve 18, to outlet port 50 of the flow member. Gas then enters pressure generator 14 through pressure generator inlet 40 and continues to respiratory circuit 12 as described above.

In the second mode gas flows from respiratory circuit port 54 to flow member outlet port 50, thereby creating a negative pressure at the respiratory circuit port 54 (e.g., for exsufflation). The gas path continues from flow member outlet port 50 through pressure generator inlet 40, into pressure generator 14. The gas leaves pressure generator 14 through pressure generator outlet 42 and flow member 16 directs gas from flow member inlet port 52 to the ambient atmosphere via valve 20.

Figure 2:
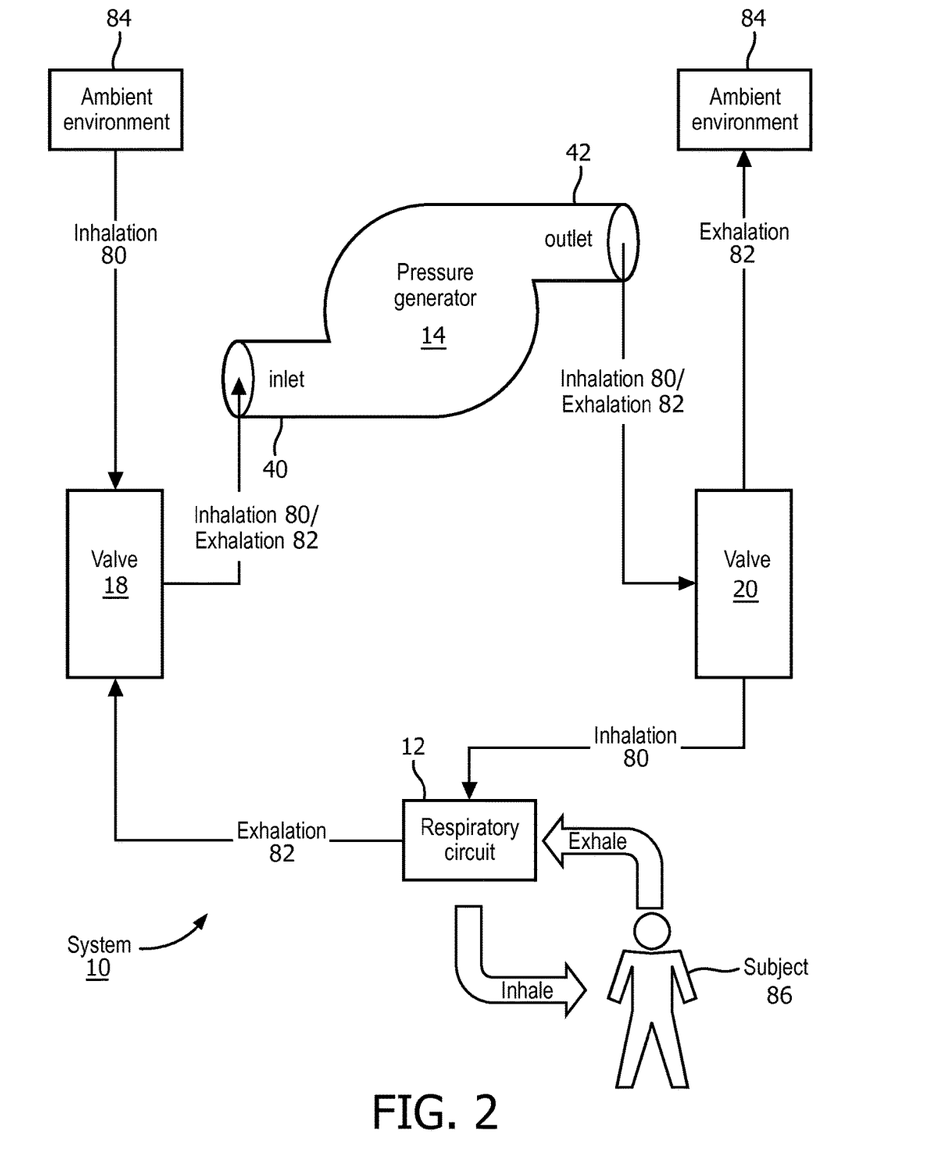
FIG. 2 is a flow schematic tracking flow through the system during inhalation and exhalation.

By way of a non-limiting example, FIG. 2 schematically maps gas flow through bi-directional flow generation system 10. Flow during inhalation 80 and exhalation 82 is shown. During inhalation 80, breathable gas flows into valve 18 from the ambient environment 84. Gas continues flowing to pressure generator 14 and a pressurized flow of breathable gas is delivered through valve 20 to a subject 86, via respiratory circuit 12. During exhalation 82, gas exhaled by subject 86 flows from respiratory circuit 12 to valve 18. Gas continues flowing through pressure generator 14, through valve 20, and into the ambient environment 84.

Returning to FIG. 1, in some embodiments, processor 24 is configured to determine one or more parameters within system 10. The one or more parameters within system 10 may comprise gas parameters related to the pressurized flow of breathable gas, breathing parameters related to respiration of a subject, and/or other parameters. Processor 24 is configured to determine the one or more parameters based on the output signals of sensors 22. The information determined by processor 24 may be used by processor 24 to control pressure generator 14, to control first valve 18, to control second valve 20, and/or for other uses.

In some embodiments, processor 24 is configured to control pressure generator 14, first valve 18, second valve 20, and/or other devices to generate the flow of gas in accordance with a ventilator regime, a positive airway pressure therapy regime, a mechanical inexsufflation regime, and/or other therapy regimes. By way of non-limiting example, processor 24 may control pressure generator 14, first valve 18, and/or second valve 20 such that the pressure support provided to the subject via the flow of gas comprises non-invasive ventilation, positive airway pressure support, continuous positive airway pressure support, bi-level support, BiPAP®, inexsufflation, and/or other types of pressure support therapy.

In some embodiments, electronic storage 26 comprises electronic storage media that electronically stores information. The electronic storage media of electronic storage 26 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 26 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 26 may store software algorithms, information determined by processor 24, information received via user a interface, and/or other information that enables system 10 to function properly. Electronic storage 26 may be (in whole or in part) a separate component within system 10, or electronic storage 26 may be provided (in whole or in part) integrally with one or more other components of system 10 (e.g., pressure generator 14, processor 24, etc.).

Figure 3:
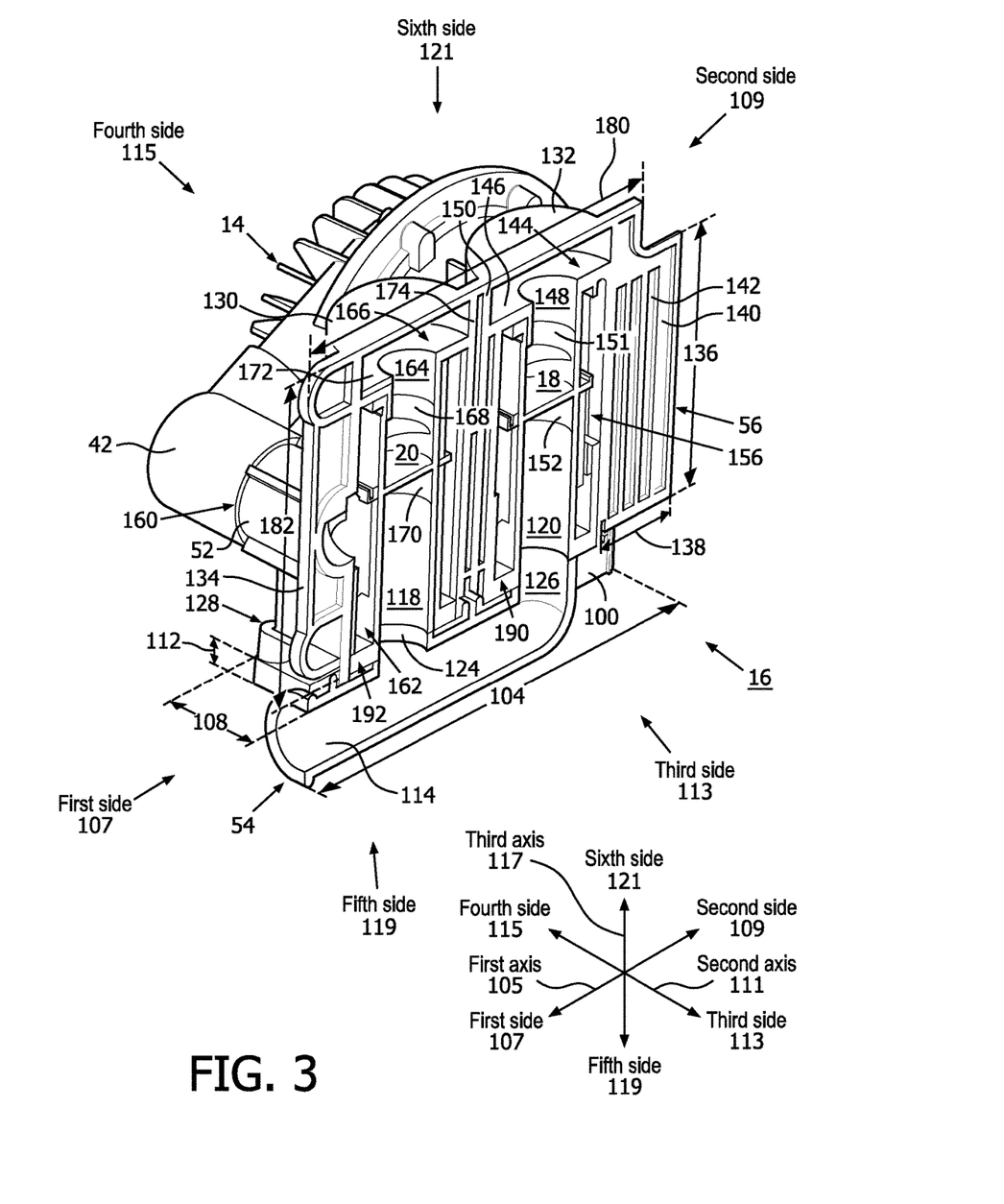
FIG. 3 is a section view of a portion of the bi-directional gas flow generation system.

FIG. 3 is sectional view of flow member 16 coupled to pressure generator 14. Flow member 16 comprises a base 100 and a manifold 102, each comprising one or more ports and/or other components.

Figure 4:
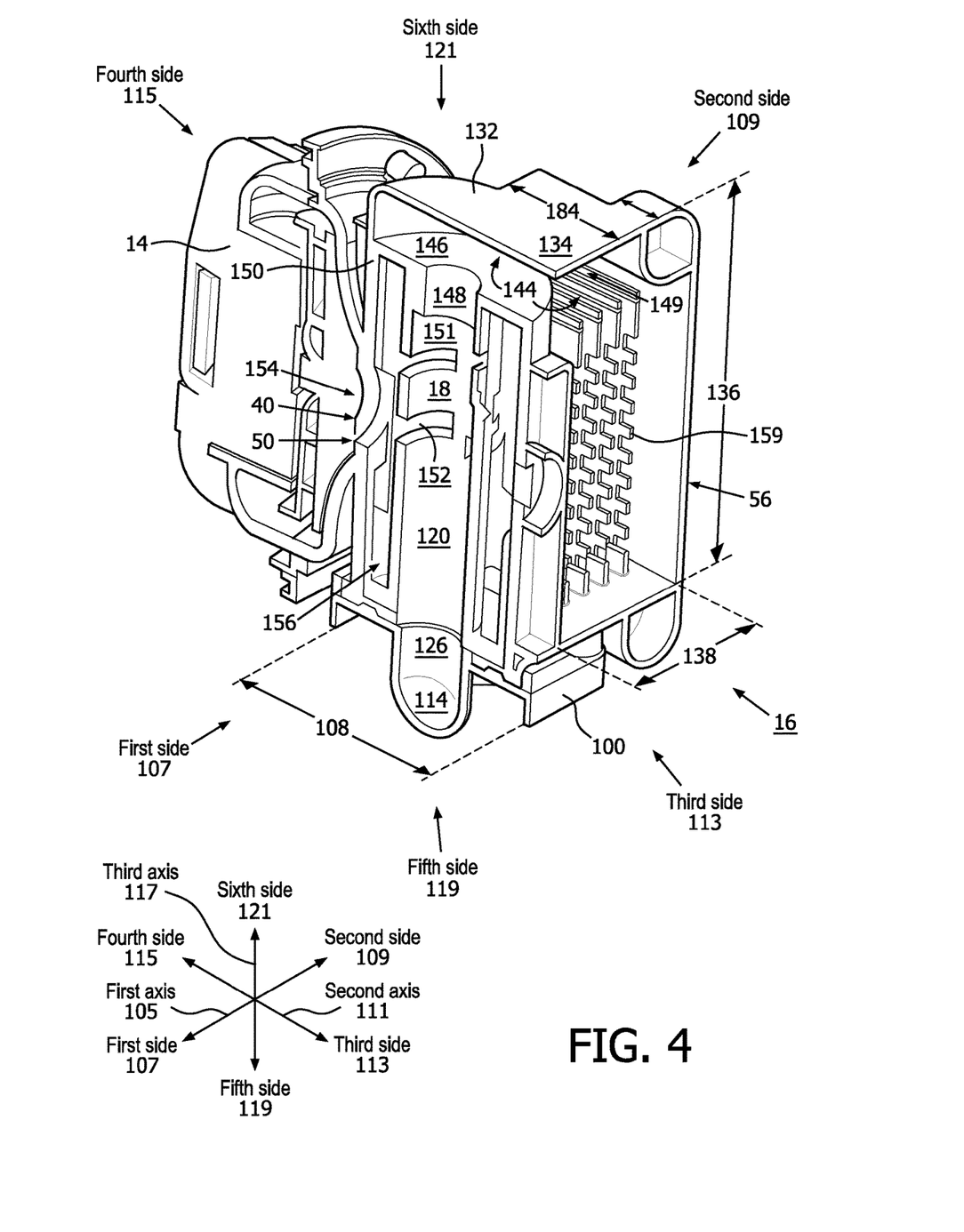
FIG. 4 is another section view of another portion of the system.

In some embodiments, base 100 is generally rectangular in shape, with a length 104 running along a first axis 105 from a first side 107 to a second side 109 of less than about 6 inches. Length 104 may be between about 5 inches and about 6 inches. Length 104 may be about 5.76 inches. In some embodiments, base 100 may have a width 108 running along a second axis 111 from a third side 113 to a fourth side 115 of greater than about 2 inches. Width 108 may be between about 2 inches and about 3 inches. Width 108 may be about 2.33 inches. (A portion of width 108 is shown in FIG. 3 because FIG. 3 is a sectional view. The full width 108 is shown in FIG. 4 described below). Base 100 has a thickness 112 running along a third axis 117 from a fifth side 119 toward a sixth side 121 of less than about 1 inch. Thickness 112 may be between about 0.1 inches and about 1 inch. Thickness 112 may be about 0.35 inches. The generally rectangular shape and approximate dimensions of base 100 shown in FIG. 3 are not intended to be limiting. Base 100 may take any shape that allows it to function as described in the present disclosure.

Respiratory circuit port 54 is formed by base 100 on first side 107 of flow member 16. From respiratory circuit port 54, a flow path 114 runs through base 100 along first axis 105 toward second side 109 of flow member 16 that is opposite first side 107. In some embodiments, flow path 114 may be generally cylindrically shaped, for example, with a radius of less than about 1 inch. The radius of flow path 114 may be between about 0.1 inches and about 1 inch. The radius of flow path 114 may be about 0.40 inches. In some embodiments, some or all of flow path 114 may have a cross section other than circular. From respiratory circuit port 54, flow path 114 extends along first axis 105 toward second side 109 of flow member 16. Toward an end of flow path 114 opposite respiratory circuit port 54, flow path 114 experiences a bend. At the end of flow path 114 opposite respiratory circuit port 54, flow path 114 forms a first orifice 126 in base 100. Between respiratory circuit port 54 and first orifice 126 along flow path 114, a second orifice 124 formed in base 100 communicates with flow path 114. Second orifice 124 faces generally in a common direction with first orifice 126.

The distance along flow path 114 from respiratory circuit port 54 to the center of second orifice 124 may be less than about 2 inches. The distance from respiratory circuit port 54 to the center of second orifice 124 may be between about 1 inch and about 2 inches. The distance from respiratory circuit port 54 to the center of second orifice 124 may be about 1.50 inches. The distance along flow path 114 between the center of second orifice 124 and the center of first orifice 126 is greater than about 2 inches. The distance between the center of second orifice 124 and the center of first orifice 126 may be between about 2 inches and about 3 inches. The distance between the center of second orifice 124 and the center of first orifice 126 may be about 2.25 inches. In some embodiments, orifices 124 and/or 126 may be generally circular shaped, for example, with a radius of less than about 1 inch. The radii of orifices 124 and/or 126 may be between about 0.1 inches and about 1 inch. The radii of orifices 124 and/or 126 may be about 0.38 inches. In some embodiments, orifices 124 and/or 126 may have a shape other than circular.

In some embodiments, manifold 102 comprises one or more flow paths, chambers, and/or other components. The shape of the outer surface of manifold 102 comprises two columns 130, 132, joined by a box 134. Column 130 and column 132 are positioned in proximity to each other along first axis 105. In some embodiments, columns 130 and/or 132 may extend from fifth side 119 of manifold 102 toward sixth side 121. In some embodiments, the distance between the center of column 130 and the center of column 132 is greater than about 2 inches. The distance between the center of column 130 and the center of column 132 may be between about 2 inches and about 3 inches. The distance between the center of column 130 and the center of column 132 may be about 2.25 inches. Column 130 is located toward first side 107 along first axis 105 and column 132 is located toward second side 109 along first axis 105. In some embodiments, columns 130 and/or 132 may be generally cylindrically, for example, shaped with a radius of less than about 1 inch. The radii of columns 130 and/or 132 may be between about 0.5 inches and about 1 inch. The radii of columns 130 and/or 132 may be about 0.96 inches. In some embodiments, some or all of columns 130 and/or 132 may have a cross-sectional shape other than circular.

Box 134 is generally rectangular in shape, with a length 180 running along first axis 105 from first side 107 to second side 109 of less than about 7 inches. Length 180 may be between about 5 inches and about 7 inches. Length 180 may be about 6.00 inches. Box 134 has a height 182 running along third axis 117 from fifth side 119 to sixth side 121 of less than about 5 inches. Height 182 may be between about 3 inches and about 5 inches. Height 182 may be about 4.00 inches. Box 134 has a width 184 running along second axis 111 from third side 113 toward fourth side 115 of greater than about 1 inch. Width 184 may be between about 1 inch and about 2 inches. Width 184 may be about 1.27 inches. (The section view in FIG. 3 does not show width 184. The section view in FIG. 4 permits a portion of width 184 to be shown). Box 134 joins columns 130 and 132 on third side 113 of manifold 102. In some embodiments, box 134 may have a general shape other than rectangular.

Flow member port 56 is located on second side 109 of manifold 102. In some embodiments, flow member port 56 may have a cross-section that is generally rectangular in shape. In some embodiments, port 56 may have a cross-sectional shape other than rectangular. Flow member port 56 is configured with a length 136 along third axis 117 from fifth side 119 of manifold 102 toward sixth side 121 of greater than about 3 inches. Length 136 may be between about 3 inches and about 4 inches. Length 136 may be about 3.12 inches. Port 56 is configured with a width 138 along first axis 105 extending from second side 109 toward first side 107 of greater than about 1 inch. Width 138 may be between about 1 inch and about 2 inches. Width 138 may be about 1.45 inches. Port 56 is configured with a depth 188 of greater than about 1 inch running along second axis 111 from third side 113 toward fourth side 115. Depth 188 may be between about 1 inch and about 2 inches. Depth 188 may be about 1.19 inches. (Depth 188 is not shown in FIG. 3. A portion of depth 188 is shown in FIG. 4). In the sectional view presented in FIG. 3, gas passes through slot openings 140 on a surface 142 of flow member port 56. (The sectional view in FIG. 4 shows baffles 159 in port 56. The arrangement of baffles 159 shown in FIG. 4 is not intended to be limiting. Baffles 159 may be arranged in any way that contributes to reducing noise in flow member port 56).

Chamber 144 comprises a hollow area inside port 56 and column 132 toward sixth side 121 of manifold 102. Chamber 144 may be confined by the wall thickness 150 of manifold 102 around column 132 and port 56. Chamber 144 is configured with a first section 146, a second section 148, and a third section 149 (shown in FIG. 4). In some embodiments, section 146 may be generally cylindrically shaped with a radius of less than about 1 inch. The radius of section 146 may be between about 0.5 inches and about 1 inch. The radius of section 146 may be about 0.88 inches. In some embodiments, section 148 may be cylindrically shaped having a radius of less than about 1 inch. The radius of section 148 may be between about 0.1 inches and about 1 inch. The radius of section 148 may be about 0.36 inches. In some embodiments, sections 146 and/or 148 may have a shape other than cylindrical.

Column 132 houses chamber 144, valve 18, flow path 120, and chamber 156. Flow path 120 extends from fifth side 119 of column 132 toward sixth side 121. Flow path 120 and chamber 144 are separated by valve 18. In some embodiments, flow path 120 may have a generally cylindrical shape with a radius of less than about 1 inch. The radius of flow path 120 may be between about 0.1 inches and about 1 inch. The radius of flow path 120 may be about 0.38 inches. In some embodiments, flow path 120 may have a length of less than about 2 inches. The length of flow path 120 may be between about 1 inch and about 2 inches. The length of flow path 120 may be about 1.71 inches. In some embodiments, the radius of flow path 120 may be substantially the same as the radius of section 148. In some embodiments, flow path 120 may have a cross-sectional shape other than circular.

Chamber 156 is bordered on sixth side 121 by chamber 144 and on fifth side by the base 190 of column 132. Chamber 156 is bordered on the outside by the wall 150 of column 132, and on the inside by the common flow path created by section 148, valve 18, and flow path 120.

Chamber 166 comprises a hollow area inside column 130 and box 134 toward sixth side 121 of manifold 102. Chamber 166 may be confined by the wall thickness 174 of manifold 102 around column 130 and box 134. Chamber 166 is configured with a first section 172, a second section 164, and a third section (located inside box 134 and not shown). In some embodiments, section 172 may be generally cylindrically shaped with a radius of less than about 1 inch. The radius of section 172 may be between about 0.5 inches and about 1 inch. The radius of section 172 may be about 0.88 inches. In some embodiments, section 164 may be cylindrically shaped having a radius of less than about 1 inch. The radius of section 164 may be between about 0.1 inches and about 1 inch. The radius of section 164 may be about 0.36 inches. In some embodiments, sections 172 and 164 may have a cross-sectional shape other than circular.

Column 130 houses chamber 166, valve 20, flow path 118, and chamber 162. Flow path 118 extends from fifth side 119 of column 130 toward sixth side 121. Flow path 118 and chamber 166 are separated by valve 20. In some embodiments, flow path 118 may have a generally cylindrical shape with a radius of less than about 1 inch. The radius of flow path 118 may be between about 0.1 inches and about 1 inch. The radius of flow path 118 may be about 0.38 inches. In some embodiments, flow path 118 may have a length of less than about 2 inches. Flow path 118 may have a length between about 1 inch and about 2 inches. Flow path 118 may have a length of about 1.71 inches. In some embodiments, the radius of flow path 118 may be substantially the same as the radius of section 164. In some embodiments, flow path 118 may have a cross-sectional shape other than circular. In some embodiments, the lengths of flow paths 118 and 120 may be substantially the same.

Chamber 162 is bordered on sixth side 121 by chamber 166 and on fifth side by the base 192 of column 130. Chamber 162 is bordered on the outside by the wall 174 of column 130, and on the inside by the common flow path created by section 164, valve 20, and flow path 118.

In some embodiments, manifold 102 is mounted to sixth side 121 of base 100. In some embodiments, manifold 102 is mounted to base 100 such that flow path 118 is coupled to orifice 124 and flow path 120 is coupled to orifice 126. Manifold 102 may be mounted to base 100 by coupling manifold 102 to the four corners 128 of base 100 with screws and/or another method of fixing manifold 102 to base 100. The method and locations for mounting manifold 102 to base 100 described in the present disclosure are not intended to be limiting. Manifold 102 may be mounted to base 100 by any method and/or in any location(s) that allows it to function as described herein.

FIG. 4 is another sectional view of pressure generator 14 and flow member 16. Pressure generator 14 is mounted to fourth side 115 of manifold 102 in a first location 154. Flow member outlet port 50 is coupled to pressure generator inlet 40. Flow member outlet port 50 is located on a fourth side 115 of cylinder 132 facing pressure generator 14. Flow member port 50 comprises chamber 156 and an orifice 158 in the wall 150 of manifold 102. Orifice 158 is coupled to pressure generator inlet 40. In some embodiments orifice 158 may have a generally circular shape with a radius of less than about 1 inch. Orifice 158 may have a radius between about 0.5 inches and about 1 inch. Orifice 158 may be about 0.86 inches. In some embodiments, orifice 158 may have a shape other than circular.

Returning to FIG. 3, pressure generator 14 is mounted to fourth side 115 of manifold 102 in a second location 160. Pressure generator outlet 42 is coupled to flow member inlet port 52. Flow member inlet port 52 is located on fourth side 115 of column 130 with the port opening facing pressure generator 14. Port 52 is configured to mate with pressure generator outlet 42. In some embodiments the opening of port 52 is cylindrically shaped with a radius of less than about 1 inch. The radius of port 52 may be between about 0.1 inches and about 1 inch. The radius of port 52 may be about 0.47 inches. In some embodiments, port 52 has a cross-sectional shape other than circular. In some embodiments, port 52 protrudes from fourth side 115 of column 130 beyond the edge of base 100.

Valve 18 is positioned between section 148 and flow path 120. A first part 151 of valve 18 is fixedly coupled to section 148. A second part 152 of valve 18 is fixedly coupled to flow path 120. Valve 18 may guide the flow of gas from flow path 118 to chamber 156 and/or from port 56 to chamber 156.

Valve 20 is positioned between section 164 and flow path 118. A first part 168 of valve 20 is fixedly coupled to section 168. A second part 170 of valve 20 is fixedly coupled to flow path 120. Valve 20 may guide the flow of gas to flow path 118 and/or to chamber 166 for eventual exit to the ambient environment.

The base, manifold, flow paths, chambers, and/or other components described above as part of FIG. 3 and FIG. 4 together form an embodiment of flow member 16 described in FIG. 1.

Figure 5:
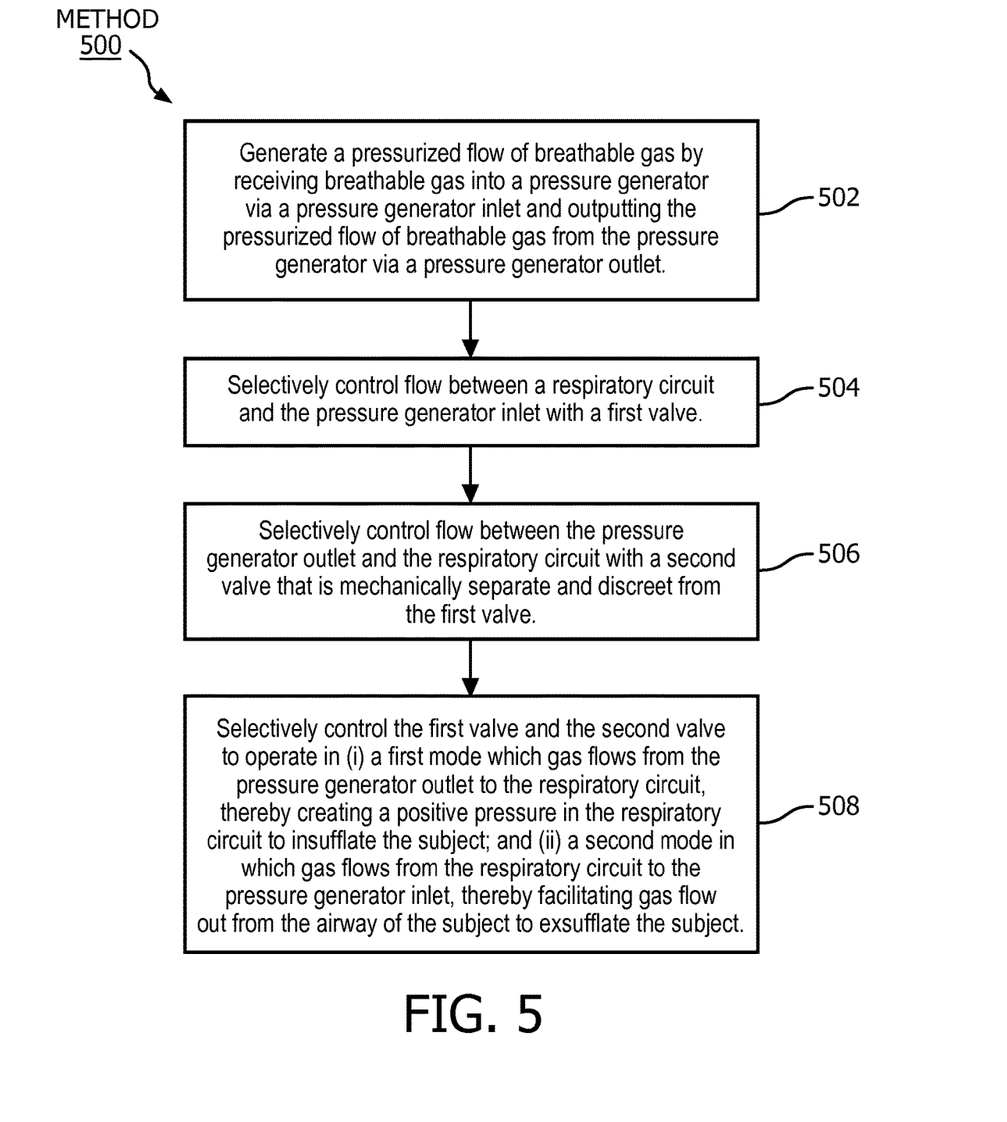
FIG. 5 is a method of generating a bi-directional flow of gas.

FIG. 5 illustrates a method 500 of generating a bi-directional flow of breathable gas. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

In some embodiments, method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At an operation 502, a pressurized flow of breathable gas is generated by receiving breathable gas into a pressure generator via a pressure generator inlet and outputting the pressurized flow of breathable gas from the pressure generator via a pressure generator outlet. In some embodiments, operation 502 is performed by a pressure generator, a pressure generator inlet, and/or a pressure generator outlet the same as or similar to pressure generator 14, pressure generator inlet 40, and/or pressure generator outlet 42 (shown in FIG. 1 and described herein).

At an operation 504, flow between a respiratory circuit and the pressure generator inlet is selectively controlled with a first valve. In some embodiments, operation 504 is performed by a valve the same as or similar to valve 18 (shown in FIG. 1 and described herein).

At an operation 506, flow between the pressure generator outlet and the respiratory circuit is selectively controlled with a second valve that is mechanically separate and discreet from the first valve. In some embodiments, operation 506 is performed by a valve the same as or similar to valve 20 (shown in FIG. 1 and described herein).

At an operation 508, the first valve and the second valve are selectively controlled to operate in (i) a first mode in which gas flows from the pressure generator outlet to the respiratory circuit, thereby creating a positive pressure in the respiratory circuit to insufflate the subject; and (ii) a second mode in which gas flows from the respiratory circuit to the pressure generator inlet, thereby facilitating gas flow out from the airway of the subject to exsufflate the subject. In some embodiments, operation 508 is performed by a processor the same as or similar to processor 24 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A bi-directional gas flow generation system, the system comprising:
   (a) a pressure generator configured to generate a pressurized flow of breathable gas for delivery to the airway of a subject, the pressure generator comprising:
      (1) an inlet configured to receive breathable gas into the pressure generator; and
      (2) an outlet configured to output the pressurized flow of breathable gas from the pressure generator;
   (b) a flow member configured to communicate with the pressure generator and a respiratory circuit, the flow member comprising:
      (1) an outlet port coupled with the pressure generator inlet;
      (2) an inlet port coupled with the pressure generator outlet;
      (3) a respiratory circuit port coupled with the respiratory circuit;
      (4) a flow path that places the respiratory circuit in fluid communication with the pressure generator, by connecting the flow member outlet port and the flow member inlet port to the respiratory circuit port;

(5) a base that includes the respiratory circuit port and a first portion of the flow path; and (6) a manifold that includes the outlet port, the inlet port, and a second portion of the flow path, wherein the flow member is configured such that the manifold is removably mounted to the base;

(c) a first valve configured to selectively control flow through the flow path between the respiratory circuit port and the flow member outlet port, the first valve included in the manifold;

(d) a second valve that is mechanically separate and discreet from the first valve, and is configured to selectively control flow through the flow path between the flow member inlet port and the respiratory circuit port, the second valve included in the manifold; and (e) a processor configured to selectively control the first valve and the second valve to operate in a first mode in which gas flows from the flow member inlet port to the respiratory circuit port, thereby creating a positive pressure at the respiratory circuit port to insufflate the subject and a second mode in which gas flows from the respiratory circuit port to the flow member outlet port, thereby facilitating gas flow out from the airway of the subject to exsufflate the subject.

2. The system of claim 1, wherein the processor is configured to selectively control the first valve and the second valve to operate in the first mode and the second mode such that the valves toggle between the first mode and the second mode to inexsufflate a subject.

3. The system of claim 1, wherein the outlet port of the flow member is directly connected to the pressure generator inlet and the inlet port of the flow member is directly connected to the pressure generator outlet.

4. The system of claim 1, wherein the flow member directs gas from the ambient atmosphere to the outlet port of the flow member responsive to the first valve and the second valve being operated in the first mode.

5. The system of claim 1, wherein the flow member directs gas from the inlet port of the flow member to the ambient atmosphere responsive to the first valve and the second valve being operated in the second mode.

6. The system of claim 1, wherein the flow member further comprises a first ambient port, and a second ambient port that each connect the flow member with ambient atmosphere.

7. A method of generating a bi-directional flow of gas, the method comprising:

(a) generating a pressurized flow of breathable gas by:
(1) receiving breathable gas into a pressure generator via a pressure generator inlet; and
(2) outputting the pressurized flow of breathable gas from the pressure generator via a pressure generator outlet;

(b) selectively controlling flow between a respiratory circuit and the pressure generator inlet with a first valve;

(c) selectively controlling flow between the pressure generator outlet and the respiratory circuit with a second valve that is mechanically separate and discreet from the first valve, wherein the pressure generator inlet and the pressure generator outlet are connected to a respiratory circuit port that is coupled with the respiratory circuit;

(d) forming the respiratory circuit port with a flow member configured to communicate with the pressure generator and the respiratory circuit, wherein forming the respiratory circuit port with the flow member comprises:
(1) coupling an outlet port of the flow member with the pressure generator inlet;
(2) coupling an inlet port of the flow member with the pressure generator outlet;
(3) coupling the respiratory circuit port with the respiratory circuit;
(4) forming a flow path that places the respiratory circuit in fluid communication with the pressure generator, by connecting the flow member outlet port and the flow member inlet port to the respiratory circuit port;
(5) forming a base of the flow member that includes the respiratory circuit port and a first portion of the flow path;
(6) forming a manifold of the flow member that includes the outlet port, the inlet port, a second portion of the flow path, the first valve, and the second valve; and
(7) removably mounting the manifold to the base; and (e) selectively controlling the first valve and the second valve to operate in a first mode in which gas flows from the pressure generator outlet to the respiratory circuit, thereby creating a positive pressure in the respiratory circuit to insufflate the subject; and a second mode in which gas flows from the respiratory circuit to the pressure generator inlet, thereby facilitating gas flow out from the airway of the subject to exsufflate the subject.

8. The method of claim 7, further comprising selectively controlling the first valve and the second valve to operate in the first mode and the second mode such that the valves toggle between the first mode and the second mode to inexsufflate a subject.

9. The method of claim 7, further comprising communicating flow between the respiratory circuit, the pressure generator inlet, and the pressure generator outlet with a flow member directly connected to the pressure generator inlet, the pressure generator outlet, and the respiratory circuit.

10. The method of claim 7, further comprising directing gas from the ambient atmosphere to the inlet of the pressure generator responsive to the first valve and the second valve being operated in the first mode.

11. The method of claim 7, further comprising directing gas from the pressure generator outlet to the ambient atmosphere responsive to the first valve and the second valve being operated in the second mode.

12. A bi-directional gas flow generation system, the system comprising:

(a) means for generating a pressurized flow of breathable gas for delivery to the airway of a subject, the means for generating comprising:
(1) means for receiving breathable gas into the means for generating; and
(2) means for outputting the pressurized flow of breathable gas from the means for generating;

(b) means for providing fluid communication between a respiratory circuit and the means for receiving and the means for outputting, wherein the means for receiving and the means for outputting are connected to a respiratory circuit port that is coupled with the respiratory circuit;

(c) first means for selectively controlling flow between the respiratory circuit and the means for receiving;

(d) second means, mechanically separate and discreet from the first means, for selectively controlling flow between the respiratory circuit and the means for outputting; and
(e) means for selectively controlling the first means and the second means to operate in (i) a first mode in which gas flows from the means for outputting, to the respiratory circuit, thereby creating a positive pressure in the respiratory circuit to insufflate the subject; and (ii) a second mode in which gas flows from the respiratory circuit to the means for receiving, thereby facilitating gas flow out from the airway of the subject to exsufflate the subject;

wherein the respiratory circuit port is formed by the means for providing fluid communication, the means for providing fluid communication comprising:
  (1) an outlet port coupled with the means for receiving breathable gas into the means for generating;
  (2) an inlet port coupled with the means for outputting the pressurized flow of breathable gas from the means for generating;
  (3) a flow path that places the respiratory circuit in fluid communication with the means for generating the pressurized flow of breathable gas, by connecting the outlet port and the inlet port of the means for providing fluid communication to the respiratory circuit port;
  (4) a base that includes the respiratory circuit port and a first portion of the flow path; and
  (5) a manifold that includes the outlet port, the inlet port, a second portion of the flow path, and the first and second means for selectively controlling flow,
    wherein the means for providing fluid communication is configured such that the manifold is removably mounted to the base.

13. The system of claim 12, wherein the means for selectively controlling the first means and the second means is configured to selectively control the first and second means to operate in the first mode and the second mode such that the first and second means toggle between the first mode and the second mode to inexsufflate a subject.

14. The system of claim 12, wherein the means for providing is directly connected to the means for receiving, the means for outputting, and the respiratory circuit.

15. The system of claim 12, wherein the means for placing directs gas from the ambient atmosphere to the means for receiving responsive to the first means and the second means being operated in the first mode.

16. The system of claim 12, wherein the means for placing directs gas from the means for outputting to the ambient atmosphere responsive to the first means and the second means being operated in the second mode.

* * * * *